United States Patent [12,076,007 B2]

(12) United States Patent
Nie et al.

(10) Patent No.: US 12,076,007 B2
(45) Date of Patent: Sep. 3, 2024

(54) REUSABLE STAPLER WITH DETACHABLE ADAPTER

(71) Applicants: Ezisurg Medical Co., Ltd., Shanghai (CN); Ezisurg (Suzhou) Medical Co., Ltd., Jiangsu (CN)

(72) Inventors: Honglin Nie, Shanghai (CN); Lei Wang, Shanghai (CN); Guang Yang, Shanghai (CN)

(73) Assignees: EZISURG MEDICAL CO., LTD., Shanghai (CN); EZISURG (SUZHOU) MEDICAL CO., LTD., Jiangsu (CN)

( * ) Notice: Subject to any disclaimer, the term of this patent is extended or adjusted under 35 U.S.C. 154(b) by 557 days.

(21) Appl. No.: 17/311,507

(22) PCT Filed: Dec. 2, 2019

(86) PCT No.: PCT/CN2019/122304
§ 371 (c)(1),
(2) Date: Jun. 7, 2021

(87) PCT Pub. No.: WO2020/114340
PCT Pub. Date: Jun. 11, 2020

(65) Prior Publication Data
US 2022/0022869 A1 Jan. 27, 2022

(30) Foreign Application Priority Data
Dec. 7, 2018 (CN) .......................... 201811492004.0

(51) Int. Cl.
*A61B 17/072* (2006.01)
*A61B 17/068* (2006.01)
*A61B 17/00* (2006.01)

(52) U.S. Cl.
CPC .......... *A61B 17/072* (2013.01); *A61B 17/068* (2013.01); *A61B 17/07207* (2013.01);
(Continued)

(58) Field of Classification Search
CPC ............ A61B 17/072; A61B 17/07207; A61B 17/068; A61B 17/115; A61B 17/32;
(Continued)

(56) References Cited

U.S. PATENT DOCUMENTS 5,467,911 A * 11/1995 Tsuruta .............. A61B 17/0684
227/19
6,032,849 A 3/2000 Mastri et al.
(Continued)

FOREIGN PATENT DOCUMENTS

CN 102038536 A 5/2011
CN 106228967 A 12/2016
(Continued)

OTHER PUBLICATIONS

International Search Report and Written Opinion mailed Feb. 3, 2020 in International Application PCT/CN2019/122304.

*Primary Examiner* — Scott A Smith
(74) *Attorney, Agent, or Firm* — Venable LLP

(57) ABSTRACT

Provided by the present invention is a reusable stapler comprising an adapter and a handle, the adapter being detachably connected to the handle. The adapter is a disposable component. The handle can be repeatedly used after being sterilized. The handle comprises a frame and an assembly/disassembly dial button, the assembly/disassembly button being mounted on the frame. The adapter comprises a center rod sleeve, the end of the center rod sleeve having a pair of bulges. The assembly/disassembly button is configured to control the detachable connection between the adapter and the handle. The handle can be repeatedly used after being sterilized, thereby reducing the surgery cost. The solution of detachable adapter provided by the present
(Continued)

invention is reliable, simple, and convenient to operate, and can effectively implement the assembly and disassembly of the adapter.

11 Claims, 5 Drawing Sheets

(52) U.S. Cl.
CPC .............. *A61B 2017/0023* (2013.01); *A61B 2017/00367* (2013.01); *A61B 2017/00473* (2013.01); *A61B 2017/00477* (2013.01); *A61B 2017/07214* (2013.01)

(58) Field of Classification Search
CPC ........... A61B 2017/07214; A61B 2017/07228; A61B 2017/00473; A61B 2017/00477; A61B 2017/2927

USPC ..... 227/19, 175.1, 176.1, 175.2; 606/1, 139, 606/219

See application file for complete search history.

(56) References Cited

U.S. PATENT DOCUMENTS

| | | | |
|---|---|---|---|
| 2016/0066912 A1* | 3/2016 | Baber | H02J 7/0068 307/64 |
| 2020/0352567 A1 | 11/2020 | Wang et al. | |

FOREIGN PATENT DOCUMENTS

| | | |
|---|---|---|
| CN | 107411793 A | 12/2017 |
| CN | 208016922 U | 10/2018 |
| CN | 208031243 U | 11/2018 |

* cited by examiner

REUSABLE STAPLER WITH DETACHABLE ADAPTER

CROSS REFERENCE TO RELATED APPLICATION

This application is a national stage application, filed under 35 U.S.C. § 371, of International Application PCT/CN2019/122304, filed on Dec. 2, 2019, entitled "REUSABLE STAPLER WITH DETACHABLE ADAPTER," which claims priority to Chinese Patent Application 201811492004.0 filed on Dec. 7, 2018 which are incorporated herein by reference in their entireties.

TECHNICAL FIELD

The present disclosure relates to a medical surgical instrument, in particular to a reusable stapler with a detachable adapter.

BACKGROUND ART

With the popularity of minimally invasive surgery, the endoscopic cutting stapler has become a conventional surgical instrument. The existing mechanical endoscopic cutting stapler relies on manual operation in the process of use, which has the disadvantages of unstable cutting, low firing force, low reliability, and laborious operation, etc., which may cause unnecessary pain or trauma to the patients during the treatment process, and also bring health risks to the hand joints of doctors who use the instrument for a long time.

There are applications of endoscopic cutting staplers in the domestic market, but they are disposable and discarded after use. Such disposable endoscopic cutting staplers, because of higher cost and higher price, bring an economic burden to the patients.

Reusable staplers have appeared in foreign markets. However, although this reusable endoscopic cutting stapler reduces the treatment cost of patients using the instruments to a certain extent, its core component handle is not suitable for repeated sterilization, and is only isolated from the patients by physical means during use and simply wiped after use to avoid cross-infection. In this way, the patients have a great risk of being cross-infected when the instrument is used for treatment.

SUMMARY

In order to solve the above-mentioned technical problems, the present disclosure provides a reusable stapler, wherein a handle of the reusable stapler is used in conjunction with a disposable adapter, which is suitable for repeated and multiple uses of the handle and reduces surgery cost. The solution of the detachable adapter provided by the present disclosure is reliable, simple, and convenient to operate, and can effectively realize the assembly and disassembly of the adapter.

According to one aspect of the present disclosure, the present disclosure provides a reusable stapler, which is used for open or endoscopic resection, transection and anastomosis of pulmonary, gastric and intestinal tissues. The stapler is composed of a handle and an adapter, and the handle can be sterilized and reused. The handle, as an important operating and executive part of the stapler, completes the firing or returns to a cutter holder, and indicates the stroke and direction of the cutter holder. The adapter is installed on the handle when in use, and a distal end of a shaft can be loaded with an appropriate staple cartridge. After completing an operation, the adapter is removed from the handle and discarded.

Further, the handle is an electric handle.

In one embodiment, the adapter and the handle are detachably connected to each other. The adapter is detachably installed on the handle at a fixed angle. The adapter is a disposable component, and the handle can be reused after being sterilized.

Further, the adapter includes a center rod sleeve, an end (a proximal end) of the center rod sleeve has a pair of bulges, the handle includes a frame and an assembly/disassembly dial button, wherein the assembly/disassembly dial button is mounted on the frame, and the assembly/disassembly dial button can control the connection between the center rod sleeve and the frame.

Further, the frame has a slot hole, and the slot hole is composed of two frame pipe walls and a pair of arc walls.

Further, the frame further has a first rib, a second rib, and a blocking wall.

Further, the assembly/disassembly dial button is provided with grooves, a toggle cap, and a restricting wall.

Further, there are two grooves, one groove is matched with the first rib on the frame, and the other groove is matched with the second rib. The assembly/disassembly dial button reciprocates back and forth along the first rib and the second rib on the frame.

Further, a limiting ring wall is further provided on the frame, and the limiting ring wall and the blocking wall define a distance of the reciprocating movement of the assembly/disassembly dial button.

Further, the adapter further includes a rotating knob, and the center rod sleeve and the rotating knob are kept as being relatively fixed during the installation process.

Further, an assembly/disassembly button is arranged on the rotating knob, and an assembly damping ring is provided at a corresponding position of the center rod sleeve.

The adapter is not easy to clean and sterilize, and the handle needs to be sterilized multiple times. The stapler with the detachable adapter not only enables the reuse of high-value core component handle and reduces the treatment cost of patients, but also greatly reduces the risk of cross-infection of the adapter during use, improves the safety and reliability of the use of the instrument, and has a simple structure, which makes the operation more convenient for doctors.

BRIEF DESCRIPTION OF DRAWINGS

The accompanying drawings, constituting a part of the specification, are used to provide a further understanding of the present disclosure and explain the present disclosure together with the specific embodiments of the present disclosure, and do not constitute as limitations on the present disclosure.

DETAILED DESCRIPTION OF EMBODIMENTS

The present disclosure is further described below in combination with specific embodiments, wherein the accompanying drawings are only used for exemplary description, only represent schematic views rather than physical diagrams, and should not be understood as limitations on the present patent. In order to better illustrate the specific embodiments of the present disclosure, some components in the accompanying drawings may be omitted, enlarged or reduced, and do not represent the size of an actual product. For those skilled in the art, it is understandable that some well-known structures in the accompanying drawings and their descriptions may be omitted. Based on the specific embodiments in the present disclosure, all other specific embodiments obtained by those ordinarily skilled in the art without creative work fall within the protection scope of the present disclosure.

For the convenience of description, "proximal end" appearing in the full text of the present disclosure refers to the end close to an operator after the operator holds the device, and "distal end" refers to the end far away from the operator after the operator holds the device.

The present disclosure provides a stapler capable of being sterilized repeatedly and used for many time and used for open or endoscopic resection, transection and anastomosis of pulmonary, gastric and intestinal tissues.

Figure 1:
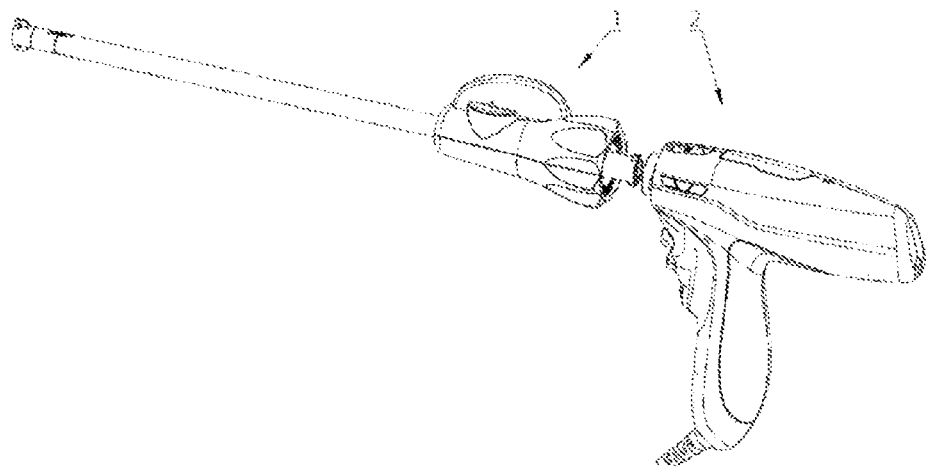
FIG. 1 is a structural schematic view of an embodiment of the present disclosure.

As shown in FIG. 1, the stapler includes an adapter 1 and a handle 2. The adapter 1 is detachably installed on the handle 2 at an angle.

Figure 2:
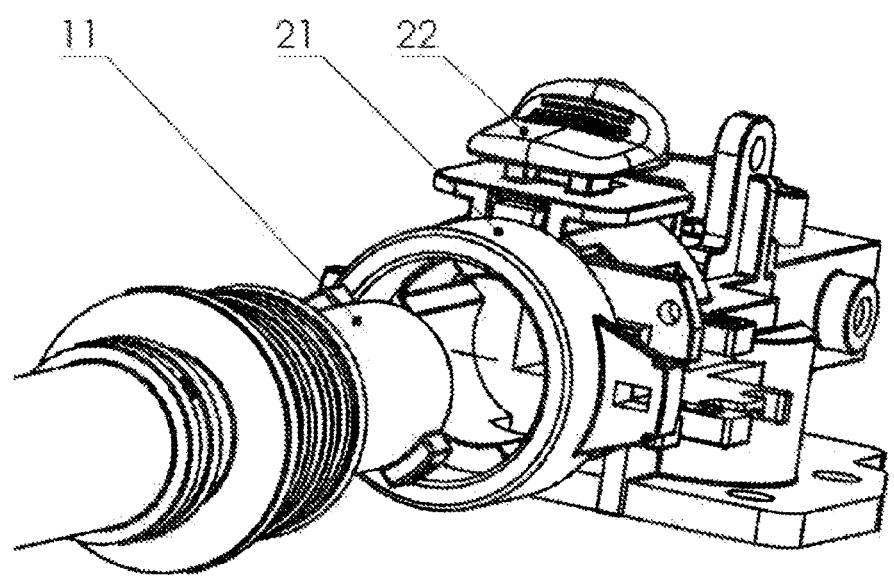
FIG. 2 is an installation schematic view of an adapter in an embodiment of the present disclosure.

As shown in FIG. 2, the adapter 1 includes a center rod sleeve 11, and the handle 2 includes a frame 21 and an assembly/disassembly dial button 22. The assembly/disassembly dial button 22 is set on the frame 21 to control the connection between the center rod sleeve and the frame.

Figure 3:
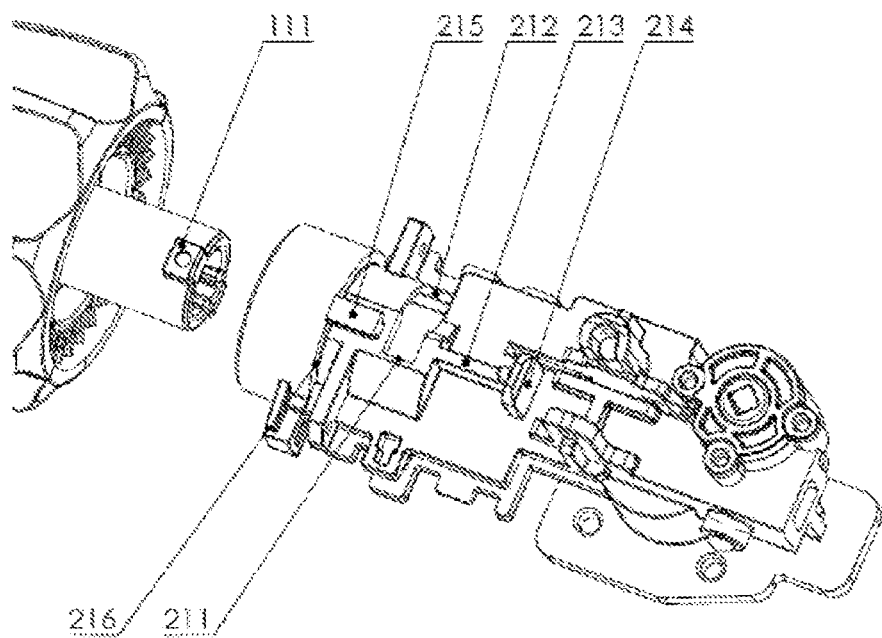
FIG. 3 is a structural schematic view of the adapter and a handle in an embodiment of the present disclosure.

As shown in FIG. 3, the adapter 1 includes a center rod sleeve 11, and an end of the center rod sleeve 11 has a pair of bulges 111. The handle 2 includes the frame 21, and the frame 21 has a slot hole composed of a frame pipe wall 212, a frame pipe wall 211 and a pair of arc walls. The frame 21 also has a first rib 215, a second rib 213, a blocking wall 214, and a limiting ring wall 216.

Figure 4:
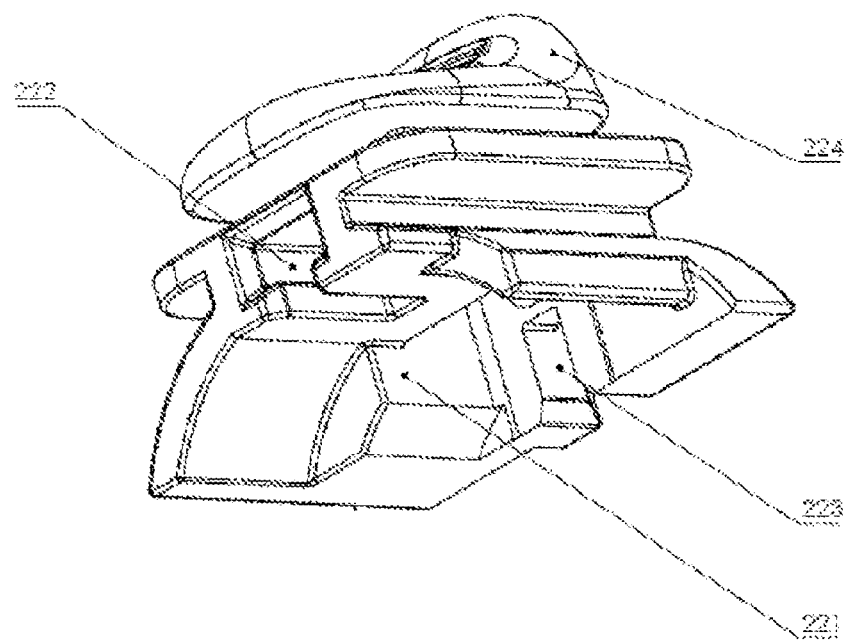
FIG. 4 is a schematic view of an assembly/disassembly dial button in an embodiment of the present disclosure.

As shown in FIG. 4, the assembly/disassembly dial button 22 has a groove 222, a groove 223, a toggle cap 224, and a restricting wall 221, wherein, the groove 222 is matched with the first rib 215 on the frame 21, and the groove 223 is matched with the second rib 213 on the frame 21. The assembly/disassembly dial button 22 reciprocates back and forth along the first rib 215 and the second rib 213 on the frame 21. The limiting ring wall 216 and the blocking wall 214 on the frame 21 define a distance of the reciprocating movement of the assembly/disassembly dial button 22.

Figure 5:
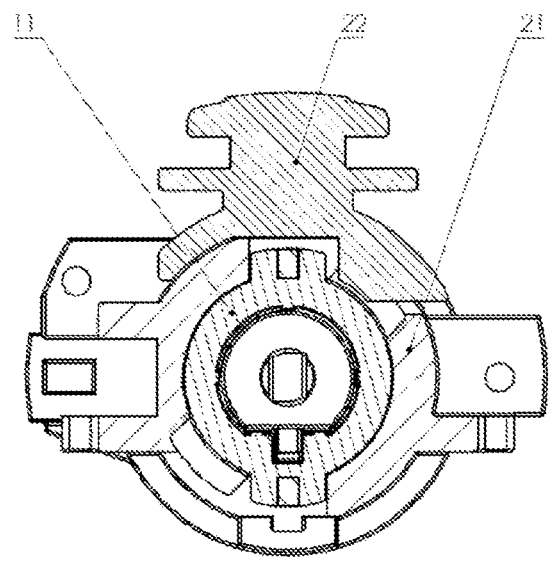
FIG. 5 is a schematic view of the adapter being installed in place in an embodiment of the present disclosure.

During the installation of the adapter 1, the center rod sleeve 11 is deflected by an angle and inserted into the frame 21 of the handle 2, and preferably, the angle is 45°. During this process, the bulges 111 pass through corresponding grooves in the frame 21, and finally reach the above-mentioned slot hole, and at the same time push the assembly/disassembly dial button 22 to the blocking wall 214. In an initial position, the bulges 111 abut against the frame pipe wall 212. And then, the center rod sleeve 11 is rotated reversely, so that the bulges 111 abut against the frame pipe wall 211. At this time, the assembly/disassembly dial button 22 automatically springs back to its original position under the action of a spring force, that is, the assembly/disassembly dial button 22 abuts against the limiting ring wall 216. At this time, the frame pipe wall 211 and the restricting wall 221 on the assembly/disassembly dial button 22 together limit the rotation of the bulges 111, so as to seize the center rod sleeve 11, so that the adapter 1 will not rotate and fall off, as shown in FIG. 5.

During the disassembly process of the adapter 1, the toggle cap 224 is pushed backward (i.e. being moved to a proximal end) so that the assembly/disassembly dial button 22 abuts against the blocking wall 214, and the assembly/disassembly dial button 22 is held. Then, the center rod sleeve 11 is rotated to make the bulges 111 abut against the frame pipe wall 212 again. At this time, the entire center rod sleeve 11 is withdrawn from the frame 21, finally the assembly/disassembly dial button 22 is released, and the adapter 1 is detached from the handle 2.

Figure 6:
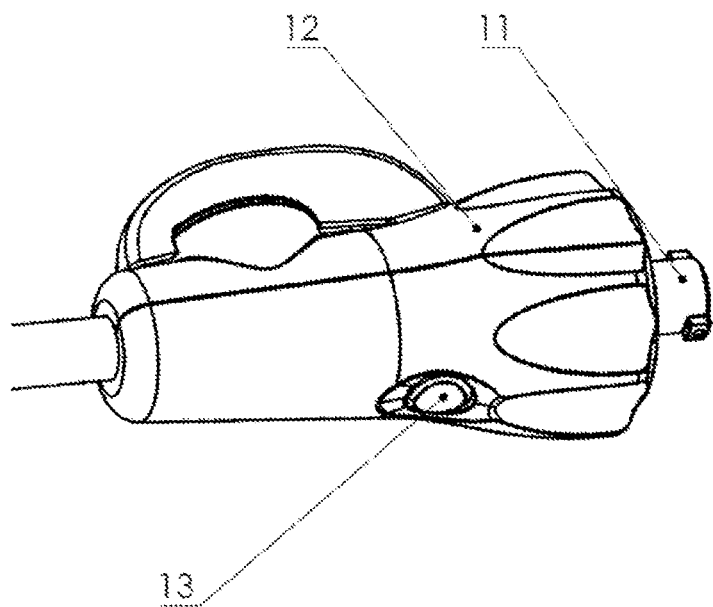
FIG. 6 is a schematic view of an assembly/disassembly button in an embodiment of the present disclosure.
Figure 7:
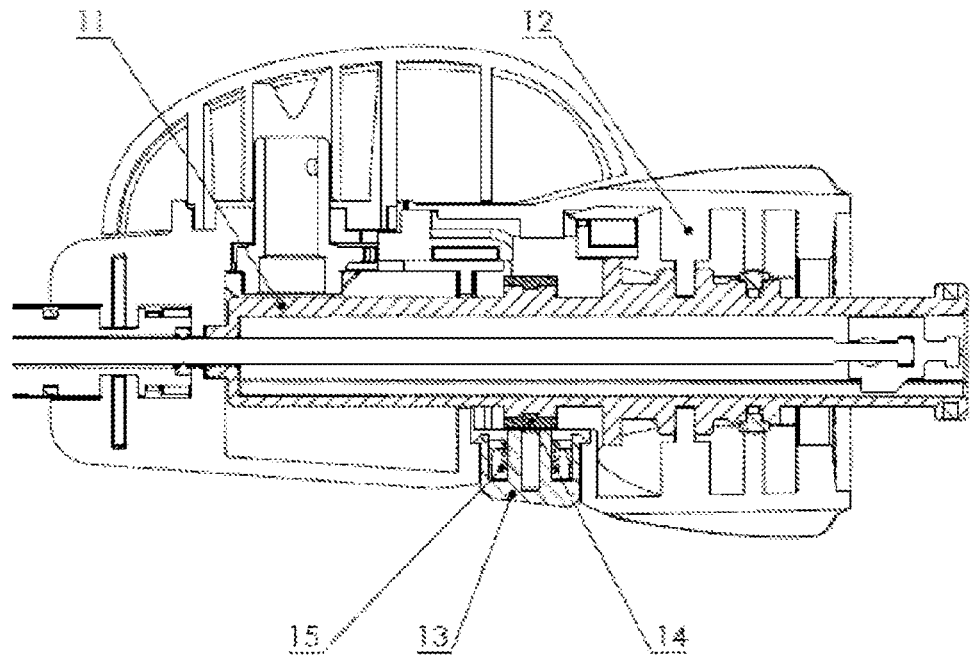
FIG. 7 is a schematic view of the interior of the adapter in an embodiment of the present disclosure.

During the use of the product, the center rod sleeve 11 and a rotating knob 12 should be able to rotate easily. However, during the installation process, the center rod sleeve 11 and the rotating knob 12 should be kept as being relatively fixed, so that the torsion force generated by the hand holding the rotating knob 12 can be transmitted to the center rod sleeve 11, to make the adapter 1 effectively installed on the handle 2. In the present disclosure, an assembly/disassembly button 13 is provided on the rotating knob 12, and an assembly damping ring 14 is provided at a corresponding position of the center rod sleeve 11, as shown in FIG. 6 and FIG. 7. During the installation process of the adapter 1, when the finger presses the assembly/disassembly button 13, under the action of the frictional force of the assembly/disassembly button 13 and the assembly damping ring 14, the center rod sleeve 11 and the rotating knob 12 are kept as being relatively fixed, so that the center rod sleeve 11 can be effectively rotated to complete the installation. After the installation is completed, the assembly/disassembly button 13 is released, the assembly/disassembly button 13 is separated from the assembly damping ring 14 under the force of a spring 15, and the center rod sleeve 11 and the rotating knob 12 are restored to have relative rotational freedom.

During the use of the product, a center rod 16 and the center rod sleeve 11 should have an axial degree of freedom. However, during the installation process, the center rod 16 and the center rod sleeve 11 should be kept as being relatively axially fixed, so that the center rod 16 has a definite position and is reliably installed on the handle 2.

Figure 8:
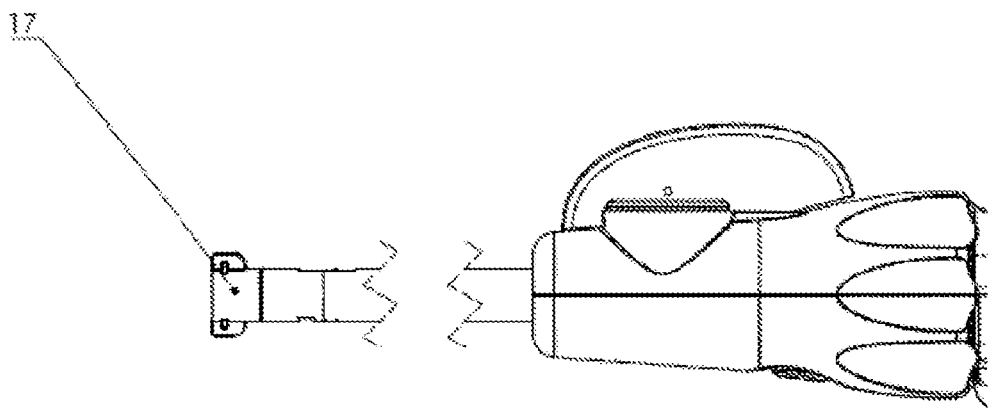
FIG. 8 is a schematic view of an assembly/disassembly accessory in an embodiment of the present disclosure.

In the present disclosure, an assembly/disassembly accessory 17 is provided at a front end (i.e. a distal end) of the adapter 1, as shown in FIG. 8.

Figure 9:
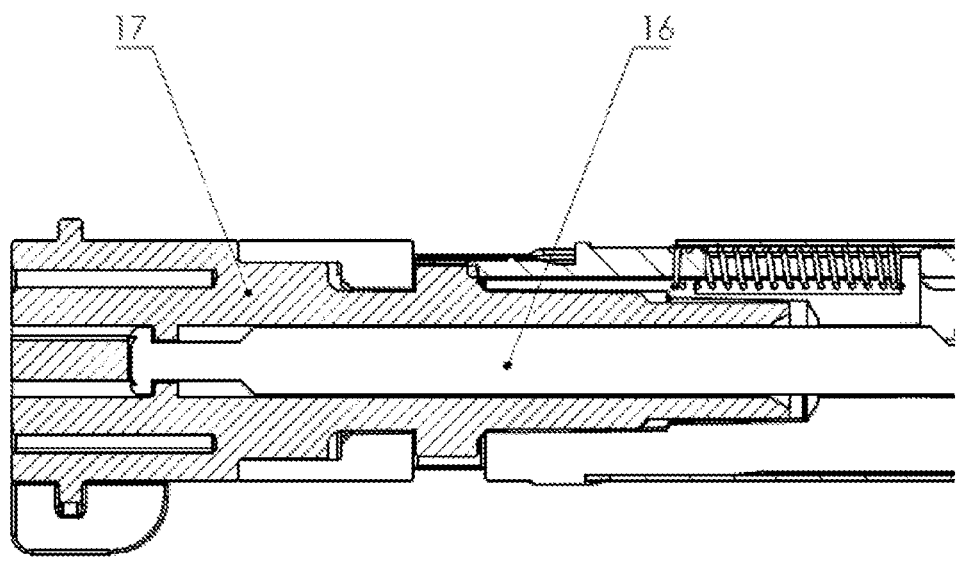
FIG. 9 is a schematic view of relative positions of the assembly/disassembly accessory and a center rod in an embodiment of the present disclosure.

The assembly/disassembly accessory 17 is assembled on the adapter 1 at the factory. A clamping groove is designed in the assembly/disassembly accessory 17, and an end (i.e. a distal end) of the center rod 16 is fixed in this clamping groove so as to determine an axial position of the center rod 16 in the adapter 1, as shown in the FIG. 9. During the process of installing the adapter 1 to the handle 2, the assembly/disassembly accessory 17 ensures a definite position of the center rod 16 in the axial direction, so that the center rod 16 can be installed in a proper position. After the installation is completed, the assembly/disassembly accessory 17 is removed, and an appropriate staple cartridge can be installed.

Although the specific embodiments of the present disclosure have been shown and described, for those ordinarily skilled in the art, it can be understood that various changes, modifications, substitutions and variations can be made to these specific embodiments without departing from the principle and spirit of the present disclosure, and the scope of the present disclosure is defined by the appended claims and their equivalents.

What is claimed is:

1. A reusable stapler, comprising an adapter and a handle, the adapter being detachably connected to the handle, wherein the adapter is a disposable component, and the handle is reusable after being sterilized;
wherein the handle comprises a frame and an assembly/disassembly dial button mounted on the frame;
wherein the adapter comprises a center rod sleeve;
wherein an end of the center rod sleeve is provided with bulges;
wherein the frame is provided with a first frame pipe wall, a blocking wall, and a limiting ring wall;
wherein the assembly/disassembly dial button is provided with a restricting wall;
wherein during an installation process of the adapter,
the center rod sleeve is inserted into the frame, and the bulges push the assembly/disassembly dial button to the blocking wall,
the center rod sleeve is rotated, so that the bulges abut against the first frame pipe wall,
the assembly/disassembly dial button springs back to abut against the limiting ring wall, and the first frame pipe wall and the restricting wall limit rotation of the bulges to seize the center rod sleeve.

2. The reusable stapler according to claim 1, wherein the frame is provided with a pair of arc walls.

3. The reusable stapler according to claim 1, wherein the frame is further provided with a first rib and a second rib.

4. The reusable stapler according to claim 3, wherein the assembly/disassembly dial button is provided with a first groove, a second groove and a toggle cap, wherein the first groove is matched with the first rib on the frame, and the second groove is matched with the second rib on the frame.

5. The reusable stapler according to claim 4, wherein the assembly/disassembly dial button is configured to reciprocate back and forth along the first rib and the second rib on the frame.

6. The reusable stapler according to claim 1, wherein the limiting ring wall and the blocking wall on the frame define a distance of reciprocating movement of the assembly/disassembly dial button.

7. The reusable stapler according to claim 6, wherein during a disassembling process of the adapter, a toggle cap is pushed backwards so that the assembly/disassembly dial button abuts against the blocking wall and the assembly/disassembly dial button is held; then, the center rod sleeve is rotated so that the bulges abut against the second frame pipe wall again, and at this time, an entirety of the center rod sleeve is withdrawn from the frame; and the assembly/disassembly dial button is released, and the adapter is detached from the handle.

8. The reusable stapler according to claim 1, wherein the adapter further comprises a rotating knob, and the center rod sleeve and the rotating knob are fixed relatively to each other during an installation process, so that a torsion force generated by holding the rotating knob is configured to be transmitted to the center rod sleeve, to make the adapter installed on the handle.

9. The reusable stapler according to claim 8, wherein an assembly/disassembly button is arranged on the rotating knob, and an assembly damping ring is provided at a corresponding position of the center rod sleeve.

10. The reusable stapler according to claim 9, wherein during an installation process of the adapter, the assembly/disassembly button is pressed, and under an action of a frictional force of the assembly/disassembly button and the assembly damping ring, the center rod sleeve and the rotating knob are fixed relatively to each other, so that the center rod sleeve is configured to effectively rotate.

11. The reusable stapler according to claim 9, wherein after an installation process of the adapter is completed, the assembly/disassembly button is released, and under an acting force of a spring, the assembly/disassembly button is separated from the assembly damping ring, and the center rod sleeve and the rotating knob are restored to be able to rotate relatively to each other.

* * * * *